United States Patent
Jeraj et al.

(10) Patent No.: US 12,260,941 B2
(45) Date of Patent: Mar. 25, 2025

(54) TOOL FOR THE COMMUNICATION OF TREATMENT OPTION RISKS AND BENEFITS

(71) Applicant: Wisconsin Alumni Research Foundation, Madison, WI (US)

(72) Inventors: Robert Jeraj, Madison, WI (US); Daniel Tyler Huff, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 289 days.

(21) Appl. No.: 17/885,054

(22) Filed: Aug. 10, 2022

(65) Prior Publication Data
US 2024/0055090 A1    Feb. 15, 2024

(51) Int. Cl.
*G16H 20/00* (2018.01)
*G06F 3/04842* (2022.01)
*G16H 50/30* (2018.01)

(52) U.S. Cl.
CPC ......... *G16H 20/00* (2018.01); *G06F 3/04842* (2013.01); *G16H 50/30* (2018.01)

(58) Field of Classification Search
CPC ..... G16H 20/00; G16H 50/30; G06F 3/04842
See application file for complete search history.

(56) References Cited

U.S. PATENT DOCUMENTS

| | | | | |
|---|---|---|---|---|
| 8,494,869 B1 * | 7/2013 | Frasher | ................. | G16H 70/20 705/2 |
| 8,762,177 B2 * | 6/2014 | Dahan | ................... | G16H 10/20 600/300 |
| 11,158,428 B1 * | 10/2021 | Siegel | ................... | G16H 50/30 |
| 2010/0100396 A1 * | 4/2010 | Daven | ................... | G06Q 10/10 715/764 |
| 2011/0105852 A1 * | 5/2011 | Morris | .................. | G06Q 10/10 600/300 |
| 2012/0047105 A1 * | 2/2012 | Saigal | .................... | G16Z 99/00 706/54 |
| 2014/0089836 A1 * | 3/2014 | Damani | ................ | G16H 20/40 715/771 |
| 2015/0178458 A1 * | 6/2015 | Pellinat | ............. | G06Q 10/0637 705/2 |

(Continued)

FOREIGN PATENT DOCUMENTS

| WO | WO-2008060751 A1 * | 5/2008 | ......... A61B 5/0002 |
|---|---|---|---|
| WO | WO-2013173903 A1 * | 11/2013 | ............ A61C 19/00 |

OTHER PUBLICATIONS

Dolan JG, Veazie PJ, Russ AJ. Development and initial evaluation of a treatment decision dashboard. BMC Med Inform Decis Mak. Apr. 21, 2013;13:51. doi: 10.1186/1472-6947-13-51. PMID: 23601912; PMCID: PMC3639808. (Year: 2013).*

(Continued)

*Primary Examiner* — Sun M Li
(74) *Attorney, Agent, or Firm* — Boyle Fredrickson, SC (57) ABSTRACT

A tool for assessing treatment options within a risk-benefit space (plotting risk against benefit) and provides a superimposed boundary indicating patient risk-benefit preference for assessment of these options. The patient risk-benefit preference can be used to identify a preferred treatment option, and interactive controls can be provided to change risk-benefit preference, risk categories, benefit categories, disease type, and the like.

17 Claims, 5 Drawing Sheets

(56) References Cited

U.S. PATENT DOCUMENTS

| | | | |
|---|---|---|---|
| 2015/0379232 A1* | 12/2015 | Mainwaring | G16H 50/70 |
| | | | 705/2 |
| 2016/0210424 A1* | 7/2016 | Di Battista | G16H 10/60 |
| 2017/0228505 A1* | 8/2017 | Allen | G06N 5/04 |
| 2018/0330059 A1* | 11/2018 | Bates | G16H 10/60 |
| 2020/0082935 A1 | 3/2020 | Sargent et al. | |
| 2020/0243194 A1* | 7/2020 | Epstein | G16H 50/30 |
| 2020/0294671 A1* | 9/2020 | Yedwab | G16H 10/60 |
| 2020/0395112 A1* | 12/2020 | Ronner | G16H 15/00 |
| 2021/0059616 A1* | 3/2021 | Abrol | A61B 5/7435 |
| 2024/0062885 A1* | 2/2024 | Ellman | G16H 40/20 |

OTHER PUBLICATIONS

Kasper J, van de Roemer A, Pottgen J, Rahn A, Backhus I, Bay Y, Kopke S, Heesen C. A new graphical format to communicate treatment effects to patients—A web-based randomized controlled trial. Health Expect. Aug. 2017;20(4):797-804. doi: 10.1111/hex.12522. Epub Dec. 16, 2016. PMID: 27981688; PMCID: PMC5513016 (Year: 2016).*

Scalia P, Schubbe DC, Lu ES, Durand MA, Frascara J, Noel G, O'Malley AJ, Elwyn G. Comparing the impact of an icon array versus a bar graph on preference and understanding of risk information: PLoS One. Jul. 23, 2021;16(7):e0253644. doi: 10.1371/journal.pone.0253644. PMID: 34297713; PMCID: PMC8301663 (Year: 2021).*

Kasper J, van de Roemer A, Pottgen J, Rahn A, Backhus I, Bay Y, Kopke S, Heesen C. A new graphical format to communicate treatment effects to patients—A web-based randomized controlled trial. Aug. 2017;20(4):797-804. doi: 10.1111/hex.12522. Epub Dec. 16, 2016. PMID: 27981688; PMCID: PMC5513016 (Year: 2016).*

Reza Fazel et al. "Strategies for defining an optimal risk-benefit ratio for stress myocardial perfusion SPECT."; Journal of Nuclear Cardiology (May/Jun. 2011): pp. 385-392.

Brian Claggett et al.; "Treatment selections using risk-benefit profiles based on data from comparative randomized clinical trials with multiple endpoints." Biostatistics 16, No. 1 (2015): pp. 60-72.

Sanjay Kaul et al.; "Benefit-risk tradeoffs in assessment of new drugs and devices." Circulation 142, No. 20 (Nov. 2020): pp. 1974-1988.

Hani O. Nasef et al.; "Optimization of the risk-benefit ratio of differentiated thyroid cancer treatment." European Journal of Surgical Oncology 44, No. 3 (2018): pp. 276-285.

Michele L. Shaffer et al.; "Joint distribution approaches to simultaneously quantifying benefit and risk." BMC medical research methodology 6, No. 1 (Oct. 2006): pp. 1-8.

Larry D. Lynd et al.; "Advances in risk-benefit evaluation using probabilistic simulation methods: an application to the prophylaxis of deep vein thrombosis." Journal of clinical epidemiology 57, No. 8 (2004): pp. 795-803.

Cristian Zanartu et al.; "A novel patient-aimed visual tool to aid in decision making in oncology." https://ascopubs.org/doi/abs/10.1200/jco.2015.33.29_suppl.21; Journal of Clinical Oncology (published online Oct. 2015): 21-21.

Brian J. Zikmund-Fisher et al.; "Improving understanding of adjuvant therapy options by using simpler risk graphics."; NIH Public Access Author Manuscript; Cancer 113, No. 12 (Dec. 2008): pp. 3382-3390.

International Search Report for International Application PCT/US2023/029208 dated Nov. 9, 2023.

* cited by examiner

TOOL FOR THE COMMUNICATION OF TREATMENT OPTION RISKS AND BENEFITS

CROSS REFERENCE TO RELATED APPLICATION

Background of the Invention

The present invention relates to a tool to assist physicians in assessing risks and benefits of multiple medical treatment options and explaining them to their patients and in particular to a tool providing a simple visualization of risk and benefits tailored to a particular patient.

Accurate physician-patient communication is a central tenet of shared decision making (SDM), an approach which encourages providers and patients to review the best available data when making treatment decisions to make informed care choices. Shared decision-making is particularly important in areas such as cancer treatment, where beneficial treatments may carry significant risks in toxicity or cost. While the physician can evaluate the technical dimensions of medical decision-making, in most cases, the final decision will be highly dependent on the patient's preferences with respect to balancing risk and benefit, increasing the complexity of the evaluation.

Decision aids (DA) for specific diseases have been developed but are not always successful. In a study of patients with incurable lung or colorectal cancer, 69%-81% of patients did not understand that chemotherapy was not at all likely to cure their cancer. In interviews of patients with acute myeloid leukemia, 74% of patients estimated their chance of cure to be greater than 50%, despite physician estimates of cure being less than 10% for 89% of patients. Weeks J C, Catalano P J, Cronin A, Finkelman M D, Mack J W, Keating N L and Schrag D 2012 "Patients' Expectations about Effects of Chemotherapy for Advanced Cancer" New England Journal of Medicine, 367 1616-25.

The complexity of the decision-making process arises from an increasing number of treatment options with different risks including not only toxicity, but also cost and inconvenience. This complexity can hamper a full understanding the options and trade-offs and thus present an obstacle to the patient and physician arriving at best treatment option.

SUMMARY OF THE INVENTION

The present invention provides a communication tool that abstracts complex trade-offs with respect to medical treatment options into a simple risk-benefit display. The risk-benefit display locates the various treatment options within a two-dimensional area simultaneously depicting both risks and benefits for each treatment option, greatly simplifying comparison. The display further allows an overlay showing the patient's risk-benefit preferences and providing a method of quickly identifying a best or best set of treatment options. Flexible and interactive setting of patient preference as well as categories of risks and benefits, allow the user to consider various alternatives.

More specifically, in one embodiment, the invention provides a tool for visualizing medical treatment options and includes a processor executing program instructions stored in a computer-readable storage medium and providing a display to receive information for a given patient characterizing a risk-benefit preference by the patient with respect to medical treatment and to provide a display of a set of multiple treatment option markers associated with different medical treatment options and arranged in a display area along a first axis according to treatment option benefits and along a second axis according to treatment option risks. The received information is used to superimpose on the display an iso-preference boundary of equal risk-benefit preference by the patient.

It is thus a feature of at least one embodiment of the invention to simplify the assessment and treatment options without obscuring individual risks and benefits and while preserving the ability to respect an individual patients' risk-benefit preference.

The iso-preference boundary may intersect at least one marker indicating a treatment option.

It is thus a feature of at least one embodiment of the invention to allow display of the iso-preference boundary to provide context for the options by anchoring it to a particular treatment option.

A treatment decision iso-preference boundary would intersect at least one treatment option marker.

It is thus a feature of at least one embodiment of the invention to demarcate a preferred treatment option based on the patient's risk-benefit preference.

The iso-preference boundary may be represented by a band having at least one of a risk extent and benefit extent of at least 5%.

It is thus a feature of at least one embodiment of the invention to visually display an indication of imprecision likely implicit in the risk-benefit preference.

The tool may further highlight treatment option markers on the iso-preference boundary and/or on a side of the iso-preference boundary of higher probability of benefit.

It is thus a feature of at least one embodiment of the invention to visually indicate preferred treatment options.

The markers may provide varying areas in the display area according to empirical uncertainty in the risk and/or benefit of a treatment option represented by the marker, with treatment options associated with larger uncertainty having larger areas.

It is thus a feature of at least one embodiment of the invention to visually display an indication of the uncertainty of the risk or benefit associated with a particular treatment option.

The first and second axes may have a range of 0 to 100%.

It is thus a feature of at least one embodiment of the invention to provide a simple, consistent, and readily understood scale that can be applied across different benefits and risks to allow comparison.

The processor may further accept an input selection of categories of benefits and may use the input selection of categories to locate the markers and the iso-preference boundary along the first axis of the display area.

It is thus a feature of at least one embodiment of the invention to allow the user to indicate specific benefits of concern, for example, but not limited to, survival time, objective response, and clinical benefit.

Likewise, the processor may further accept inputs of categories risks and use the input selection of categories to locate the markers and the iso-preference boundary along the second axis of the display area.

It is thus a feature of at least one embodiment of the invention to allow the user to indicate specific risks of concern, for example, but not limited to, any adverse medical event, adverse medical events over a predetermined threshold, and specific organ toxicities.

In some cases, the categories maybe selected from the group consisting of: direct cost to the patient and indirect cost to the patient.

It is thus a feature of at least one embodiment of the invention to capture countervailing considerations with respect to treatment options that go beyond toxicities.

The information for a given patient characterizing the risk-benefit preference by the patient maybe entered by an interactive control manipulable by the user.

It is thus a feature of at least one embodiment of the invention to allow improved comprehension of the display of treatment options by allowing perturbation or change in the assumptions of risk-benefit.

The processor may further execute to display multiple markers associated with a given medical treatment option over different times during a patient treatment with the given medical treatment option indicating a change in the risk-benefit of the given medical treatment option informed by patient experience with respect to a given treatment.

It is thus a feature of at least one embodiment of the invention to provide a tool that can be used on an ongoing basis to determine whether a treatment option is satisfying a patient's risk-benefit preference.

The processor may further accept inputs of medical procedure categories and provides a display of a set of multiple treatment options according to an input of a medical procedure category.

It is thus a feature of at least one embodiment of the invention to provide a tool that can work with a variety of different disease categories.

The processor may further receive patient-specific clinical information for a given patient, and the treatment option risks or benefits for the treatment options may be based on the patient-specific information.

It is thus a feature of at least one embodiment of the invention to tailor the risk and benefits to known patient clinical information such as age and gender.

The processor may further receive a user-selectable maximum risk level and a minimum benefit level and may display only markers associated with treatment option benefits above the minimum benefit level and treatment option risks below the maximum risk level.

It is thus a feature of at least one embodiment of the invention to permit further simplification of the display for a patient by removing outlier treatments.

These particular features and advantages may apply to only some embodiments falling within the claims and thus do not define the scope of the invention.

DETAILED DESCRIPTION OF THE PREFERRED EMBODIMENT

Figure 1:
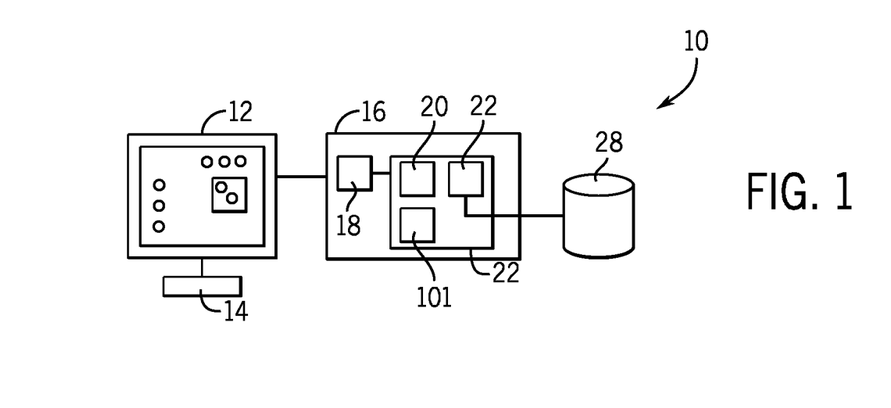
FIG. 1 is a simplified block diagram of an electronic computer suitable for use with present invention providing a processor communicating with an electronic memory holding an executable program and multiple data files and further communicating via the user terminal providing a graphic display and user input interface.

Referring now to FIG. 1, an apparatus for displaying medical treatment options 10 may provide a graphic display 12, for example, an LCD monitor or the like, but also include a static display system such as printers on which graphic images can be generated and presented to a user. The apparatus 10 further includes a user input 14, for example, a keyboard, mouse, trackball, or touchscreen overlay for receiving information related to medical treatment.

The graphic display 12 and user input 14 may communicate with an electronic computer 16, for example, having one or more processors 18 that may execute a stored program 20 held in an associated electronic memory 22. The execution of the stored program 20 may also make use of a stored data file 24.

Figure 2:
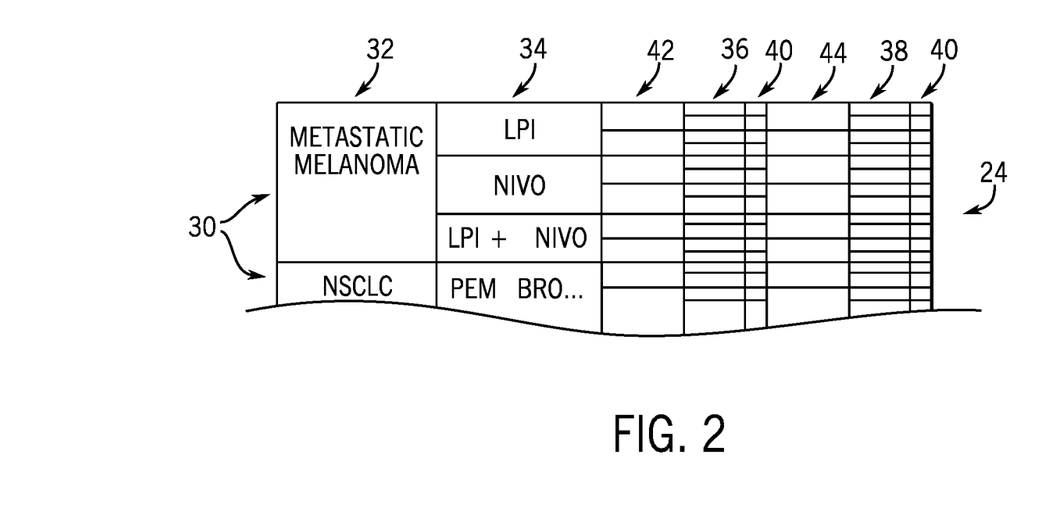
FIG. 2 is a logical diagram of a data file of FIG. 1 showing organization and categorization of medical procedures' risks and benefits.

Referring now to FIG. 2, stored data file 24 may provide for a data structure providing the risks and benefits of different medical procedures. Logically, the data file 24 may be organized for retrieval, for example, as a database, having a set of rows 30 and columns linking medical procedures, risks, benefits, patient information and the like. For example, a first column may provide medical conditions 32. For example, the medical conditions 32 may include but not be limited to: Metastatic Melanoma, Non-Small Cell Lung Cancer (NSCLC), and Metastatic Castration-Resistant Prostate Cancer (mCRPC) as depicted in this example. Within each of these categories of medical conditions 32 and as indicated by a second column, multiple treatment options 34 may be listed, in this example including but not limited to treatment options using Ipilimumab, Nivolumab, Ipilimumab plus Nivolumab, or Pembrolizumab.

For each of these treatment options 34, a set of risks 36 and benefits 38 indicated by corresponding columns may be provided.

These risks 36 may in turn be categorized, for example, as adverse medical events, or nonmedical risks such as cost, and may denote a probability from 0 to 100% indicating the chance of realizing that risk. Each of these categories of risks 36 can be further subdivided; for example, the category of adverse medical events can be subdivided into adverse medical events, only serious adverse medical events according to some predefined standard, or specific organ toxicities such as colitis or pneumonitis. Similarly, the cost category of risks 36 can be subdivided into direct costs (for example, payments for medical services and supplies borne by the patient) and indirect costs (for example, burdens in time, opportunity cost from work absence, travel to the treatment site, etc.) and each category further subdivided to dollar thresholds. Generally, these risks 36 for each of these categories may be determined through literature studies or surveys and may each be associated with an empirical uncertainty value 40. The number of categories may change depending on available information.

In a similar way, the benefits 38 may be organized in the various subcategories, for example, being survival fraction at a user-selected time cutoff (e.g., proportion of patients surviving at 12 months), objective response rate (the proportion of lesions achieving a shrinkage in tumor size), and clinical benefit (the proportion of patients benefiting from treatment and continuing on therapy by clinical assessment). Like the risks, the benefits may also be subdivided, for example, providing benefits broken down into different ranges of survival time, again each benefit or subcategory being assigned a probability from 0 to 100% derived from literature searches or the like, and may be associated with an empirical uncertainty value 40.

The initial risk-benefit assessments are population-based average risk-benefits, while each individual patient can be different from this average. For this reason, the risks 36 and the benefits 38 may be further associated with patient-specific risk factors 42 and patient-specific benefit factors 44 that can modify the risks 36 and benefits 38 according to patient-specific clinical information such as gender, age, genetic markers, radiological imaging findings, and various biomarkers (e.g., molecular biomarkers, imaging biomarkers), blood tests, genomic data, radiological images, patient risk factors, family history, or the like. Again this information can be extracted from empirical studies or literature searches and will generally be updated from time to time as stored in the data file 24.

Figure 3:
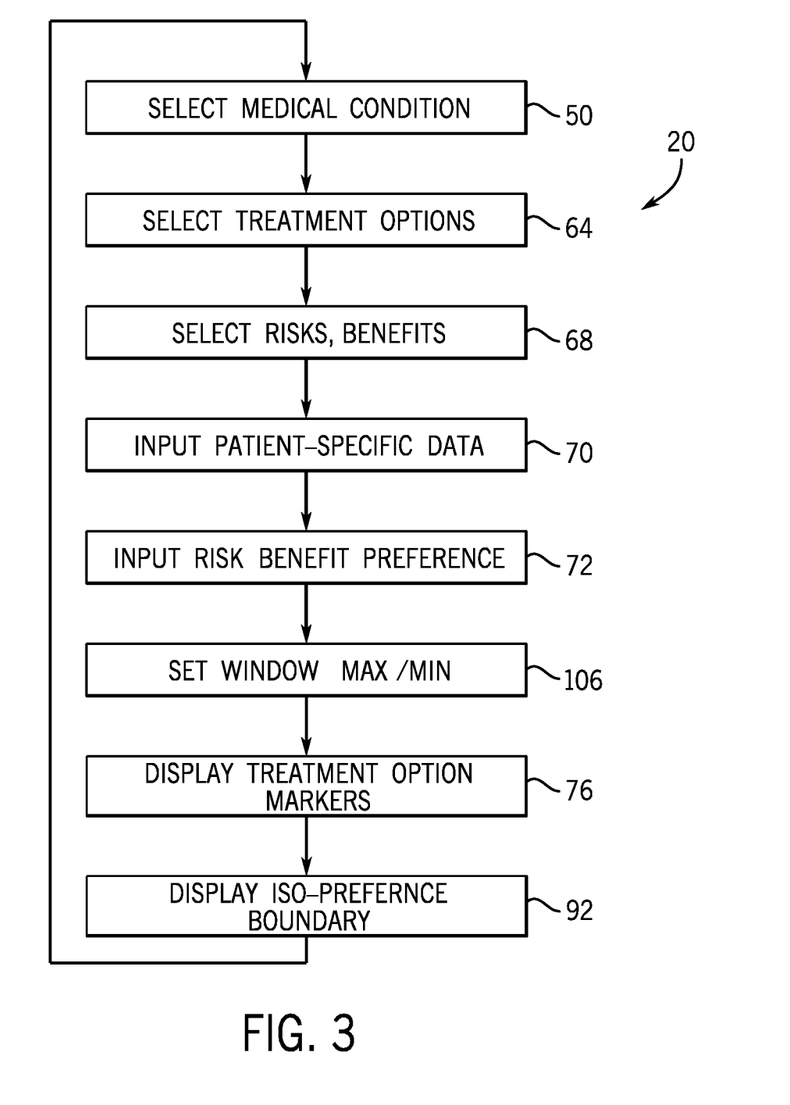
FIG. 3 is a flowchart showing the principle steps of the executable program of FIG. 1.
Figure 4:
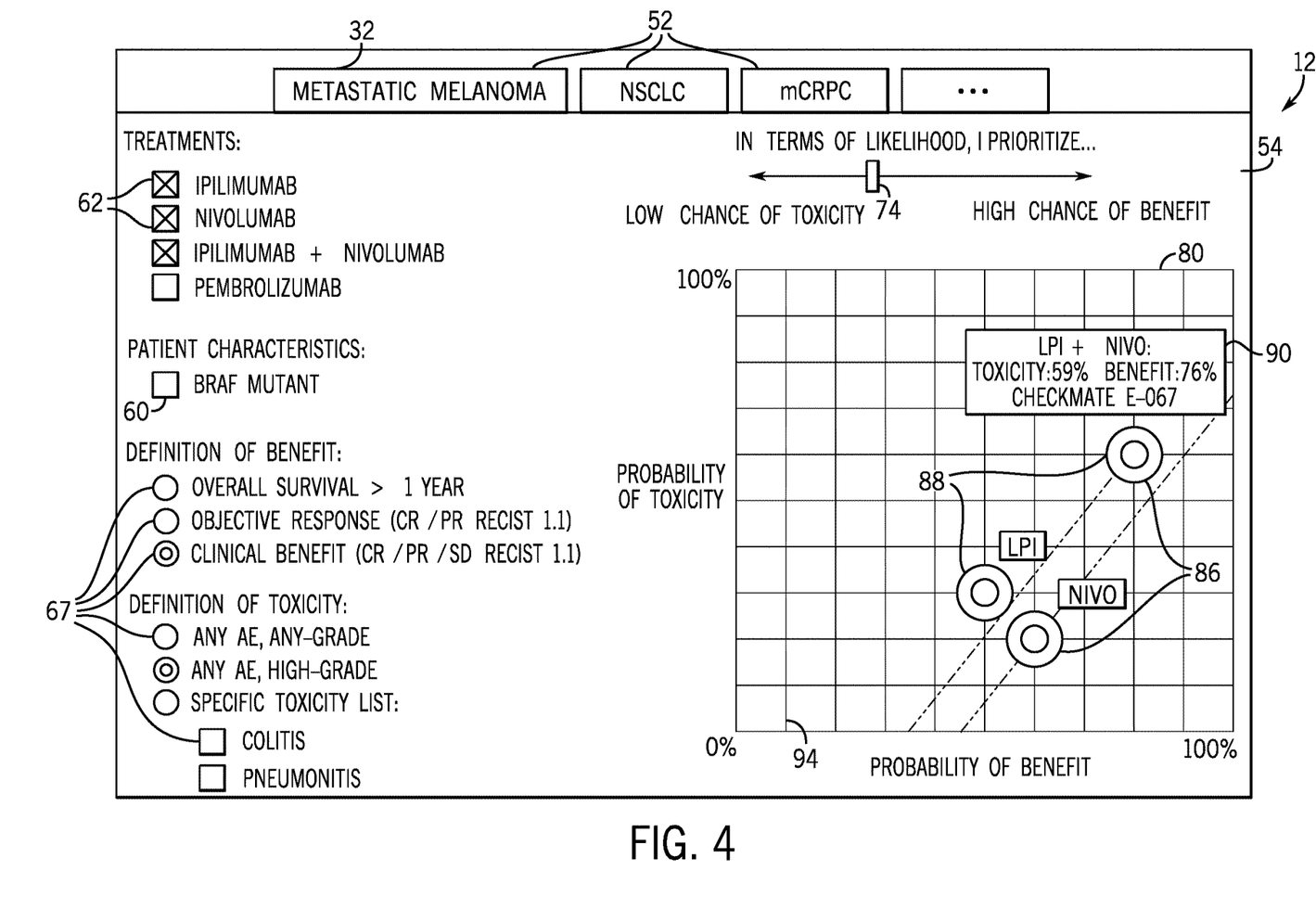
FIG. 4 is an example screen display produced on the graphic display and showing multiple markers associated with treatment options arranged in a risk-benefit space, the latter also showing an iso-preference boundary being a locus of equal risk-benefit preference points for a given patient and further showing user controls for various inputs for defining risks and benefits and the risk-benefit preference of the patient.

Referring now also to FIGS. 3 and 4, the program 20 may begin execution as indicated by process block 50 by accepting from the physician or a patient an input of a medical condition 32, for example, metastatic melanoma, in this example by selecting a tab 52 on a display 54 output on display 12.

Based on the selected medical condition 32, and as will occur upon each input step, the display 54 will update appropriately, in this case to show a set of possible treatment options 34 for the medical condition 32 each identified by a check box 62 or other input method. All or some of these treatment options 34 may be selected by the user and an input received according to process block 64.

Based on the selection of the medical condition 32 and treatment options 34, the display 54 will update to indicate patient-specific risk factors 42, patient-specific benefit factors 44, and particular benefits 38 and risks 36 associated with those treatments 62 and that medical condition 32, for example, each of these options assigned to check boxes 60 and 67 as depicted. Per process blocks 68 and 70, particular patient-specific risk factors 42 or patient-specific benefit factors 44 and particular categories of risk 36 and benefit 38 may be selected and received as inputs by the program 20. In this example, the risks 36 as depicted are only medical risks; however, the invention contemplates categories of cost, etc. may also be considered as risks and presented.

Per process block 72 of FIG. 3, the program 20 may then receive a patient risk-benefit preference 101 (shown in FIG. 1 after storage in the electronic memory 22) representing the patient's attitude with respect to a trade-off between risks 36 and benefits 38 of the type selected. In one embodiment, this preference may be obtained, for example, using a slider 74 on a display for output to the display 12 manipulated by the user. This slider 74 importantly provides an interactive qualitative way to input the patient preferences that require a trading off of risk and benefit (that is both low risk and high benefit cannot be obtained at once). The slider 74 may be labeled dynamically according to the risks 36 and benefits 38 selected and, accordingly, in this example, show a trade-off between benefits and toxicity (rather than a more general risk) tailored to the fact that only toxicity risks were selected. Alternate methods of reducing patient risk-benefit preference 101 are contemplated, for example, through questionnaires of the patient, for example, providing for revealed preferences by the patient according to a set of questions or the like.

As indicated by process block 76, the above entered information may then be used to prepare a risk-benefit map 80 having perpendicular axes of benefit probability from 0 to 100% (in this case the horizontal axis) and risk probability (in this case the vertical axis) graduated in linear scales of 0 to 100%. For each of the identified treatment options per check boxes 62, a marker 86 will be placed on the risk-benefit map 80 according to the associated risk 36 and benefit 38 of that treatment option from data file 24. In this way, markers 86 for treatment options with higher benefit will be positioned further to the right on the risk-benefit map 80 as depicted, and treatment options with higher risk of toxicity will be placed higher on the risk-benefit map 80 as depicted.

Each marker 86 may be sized or associated with a halo 88 having an area or linear dimension dependent on the uncertainty in the probability of risk 36 and benefit 38 measurement associated with that treatment option. In this way, treatment options having greater uncertainty in their outcome will exhibit a larger halo 88 serving in the manner of an error bar in two dimensions. Each of the markers 86 may also be associated with a caption 90 indicating the name and possibly other data about the treatment option as desired.

The location of the markers 86 on the risk-benefit map 80 provides an immediate and intuitive visual representation of the trade-off between risks and benefits with the user able to see not only which is the most beneficial treatment or which treatment has the lowest risks but how these different factors relate to each other.

To further assist in this assessment of treatment options and as indicated by process block 92, an iso-preference boundary 94 may be superimposed on the risk-benefit map 80 indicating a line or region of points on the risk-benefit map 80 to which the particular patient should be indifferent based on their risk-benefit preference 101. In this example, this preference is considered to be linear; however, it will be appreciated that any monotonic function between risk and benefit may be displayed in this matter.

The iso-preference boundary 94 provides a finite width (both in risk and benefits) that is intended to reflect the fact that there is likely uncertainty by any individual with respect to a risk-benefit preference and, accordingly, a width of at least 5% and typically 10% may be provided. This width maybe implemented either by a thickened boundary line or by a gradient of shading, for example, progressively darker shading proceeding downward into the right from the boundary's leftmost edge in the risk-benefit map 80 as depicted.

While multiple iso-preference boundaries 94 may be generated in the manner of a topographical map, in one embodiment a single iso-preference boundary 94 will be anchored to a particular marker 86, this single iso-preference boundary 94 reflecting a particular underlying cost function which may, for example, be represented as:

$$C = w_B(1-P_B) + w_T p_T$$

where $p_B$ and $p_T$ are the likelihoods of benefit and toxicity associated with that treatment option and weights $w_B$ and $w_T$ define the patient risk-benefit preference 101.

For a patient with low risk tolerance, avoiding toxicity is the priority, so a higher $W_T$ relative to $w_B$ is assigned. For a patient with high risk tolerance, benefit from treatment is the priority, so higher $w_B$ relative to $w_T$ is assigned. To fairly compare cost function values across varying patient risk tolerances, the weights observe the constraint:

$$W_B + W_T = 1.$$

Figure 5:
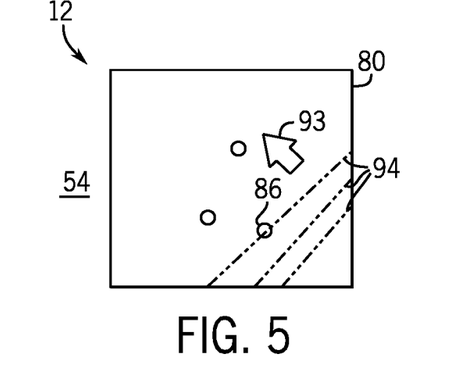
FIG. 5 is a simplified representation of the risk-benefit map of FIG. 4 showing placement of a location of the iso-preference boundary.

Referring now to FIG. 5, graphically, a determination of the particular marker 86 to which the iso-preference boundary 94 is anchored can be considered a process of moving through iso-preference boundaries starting at the right side of the risk-benefit map 80 and moving leftward through boundaries (as indicated by arrow 92) until a boundary is reached that first intersects a marker 86. This progression to the left can be thought of as gradually increasing the cost C. The first marker 86 that is intersected is "optimal" for this patient from a risk-benefit standpoint—it is the treatment option which minimizes C.

It will be understood that the slider 74 and the various check boxes (or similar controls) 62, 60 and 67 may be interactively adjusted while watching the risk-benefit map 80 to experiment with different alternatives and to provide the user with an understanding of the interaction of these decisions.

Figure 6:
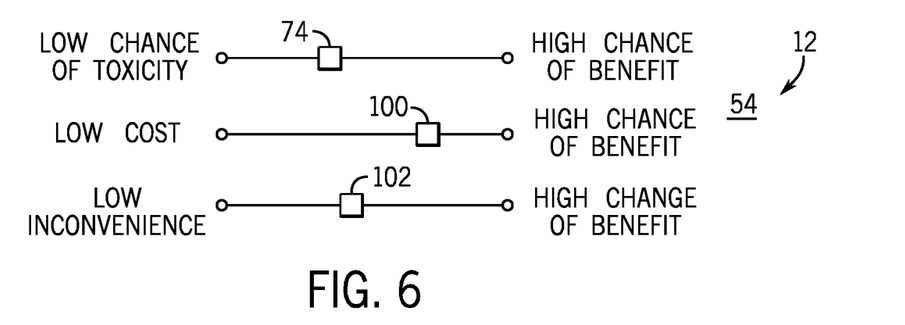
FIG. 6 is a fragmentary view of FIG. 4 showing multiple user controls for providing a risk-benefit reference comprised of medical and nonmedical risks and benefits.

Referring now to FIG. 6, the patient's risk-benefit preference established via slider 74 may be expanded to include multiple dimensions, for example, not only medical risks per slider 74 but also costs per a slider 100 and inconvenience (nonpecuniary costs) per slider 102. In one embodiment, each of these of these sliders 74, 100, and 102, may contribute a pair of weights $w_B$ and $w_T$ which can be averaged together or otherwise combined per the cost function discussed above.

Figure 7:
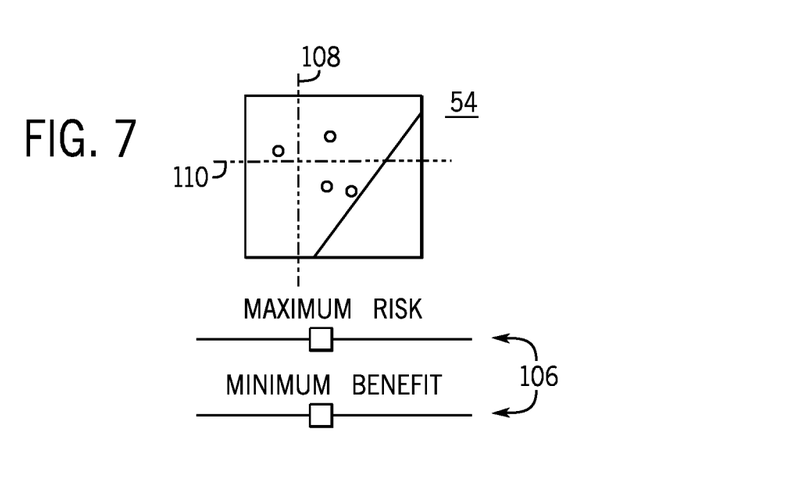
FIG. 7 is a simplified representation of the risk-benefit map of FIG. 4 showing inputs to define maximum risk and minimum benefit.

Referring now to FIGS. 3 and 7, it may be desirable to limit the extent of the risk-benefit map 80, for example, to exclude treatment possibilities that have extremely high risks or extremely low benefits. Referring to process block 106, in this regard, the display 54 may provide additional sliders 106 (shown in FIG. 7) or similar controls defining a required minimum benefit 108 or defining a maximum risk 110 for any treatment option which will have a marker 86 displayed. According to the settings, markers 86 associated with treatment options having higher risks than maximum risk 110 or lesser benefit than minimum benefit 108 will be excluded from display 54 and from the risk-benefit map 80.

Figure 8:
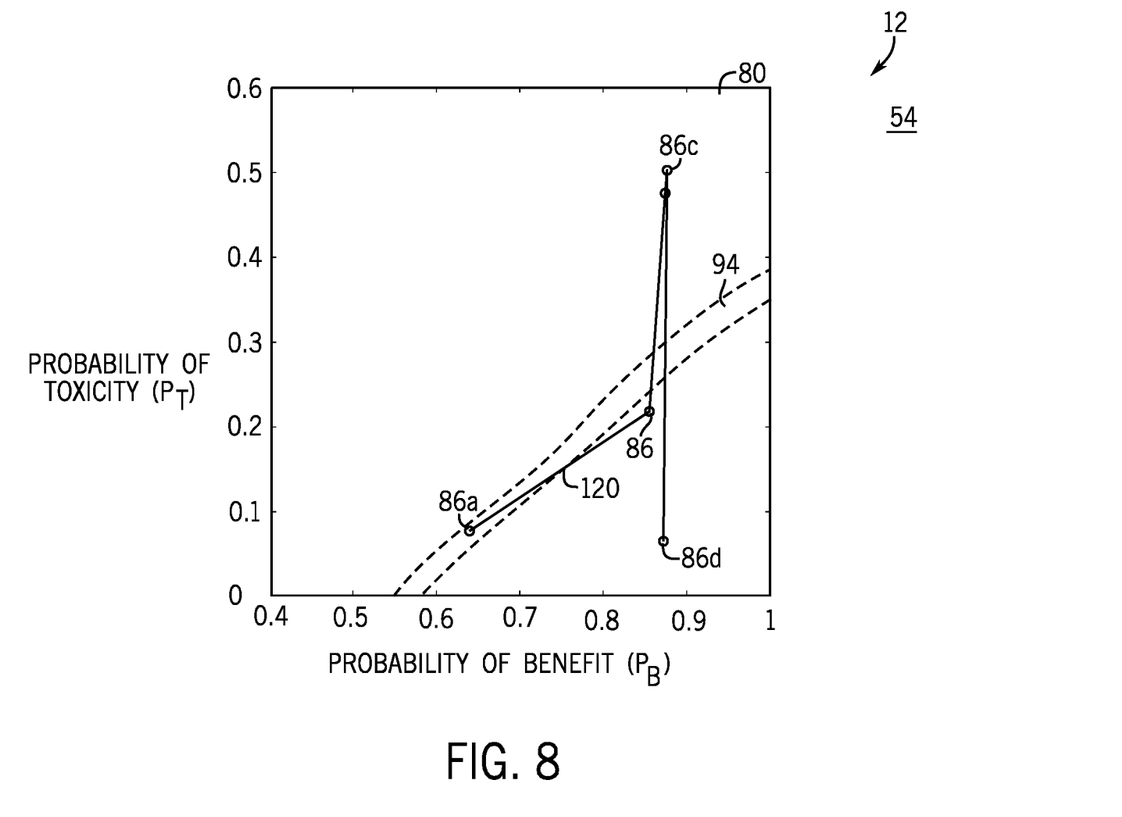
FIG. 8 is a simplified view of the display of FIG. 4 showing a trajectory of a given marker over a span of a patient treatment displayed with respect to the patient's iso-preference boundary and useful for reassessing treatment option.

Referring now to FIG. 8, once a given treatment option is selected with consultation to the risk-benefit map 80, the display 54 may serve an additional function of tracking risk and benefits of the actual treatment option selected as may change during treatment of the patient. In this case, the initial marker 86 (represented as 86a) used to select the treatment option from among other treatment options may be retained on the risk-benefit map 80 together with the corresponding iso-preference boundary 94. As treatment progresses, additional markers 86b-86c may be placed on the risk-benefit map 80 having different positions in terms of risks and benefits as a result of refined understanding of the risks and benefits and patient-specific response to a particular treatment. For example, if the disease burden reduces with treatment, the benefit after that treatment indicated by marker 86b and risk of toxicity effects which may not have realized may be less.

Assessment of treatment efficacy and toxicity during treatment, for example, may be performed using the techniques described in US patent application 2014/0276035 "System and Method for Evaluation of Disease Burden"; 2016/0100795 "System and Method for Evaluation of Disease Burden"; 2018/0330495 "Image Enhancement System for Bone Disease Evaluation" and 2021/0345957 "Apparatus for Monitoring Treatment Side Effects" all assigned to the assignee of the present invention and hereby incorporated by reference.

The various markers 86a-86d together provide a trajectory 120 that can be used to monitor and/or modify the treatment of the patient, for example, reducing treatment doses when the trajectory 120 is veering to outside of the iso-preference boundary 94 or, in this case, when marker 86c is evaluated. This information may also be used in future treatments to anticipate the possible progression of benefits and risks.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a computer" and "a processor" or the like can be understood to include one or more computers that can communicate in a stand-alone and/or a distributed environment(s), and can thus be configured to communicate via wired or wireless communications with other processors, where such one or more processors can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A tool for visualizing the risks and benefits of multiple medical treatment options and comprising:
 a processor providing an electronic database of risks and benefits of different treatment options and executing program instructions stored in a computer-readable storage medium and providing a display to:
 (a) receive information for a given patient characterizing a risk-benefit preference by the patient with respect to medical treatment;
 (b) access the database to provide a display of a set of multiple treatment option markers associated with different medical treatment options and arranged in a display area along a first axis according to treatment option benefit and along a second axis according to treatment option risk; and
 (c) use the received information to interactively superimpose on the display area an iso-preference boundary of equal risk-benefit preferences by the patient.

2. The tool of claim 1 wherein the iso-preference boundary intersects at least one marker indicating a treatment option.

3. The tool of claim 2 wherein the iso-preference boundary is an iso-preference boundary intersecting at least one marker.

4. The tool of claim 2 wherein the iso-preference boundary is represented by a band having at least one of a risk-extent and benefit-extent of at least 5%.

5. The tool of claim 1 wherein the processor further executes to highlight markers on the iso-preference boundary and/or on a side of the iso-preference boundary of having lower-cost function values, the cost function relating risks and benefits of a treatment option weighted according to patient risk-benefit preference.

6. The tool of claim 1 wherein the markers provide varying areas in the display area according to empirical uncertainty in the probability of risk and benefit of a treatment option represented by the marker with treatment options associated with larger uncertainty having larger areas.

7. The tool of claim 1 wherein the first and second axes have a range of 0 to 100%.

8. The tool of claim 1 wherein the processor further accepts an input selection of categories of benefits and uses the input selection of categories to locate the markers and the iso-preference boundary along the first axis of the display area.

9. The tool of claim 8 wherein the categories are selected from the group consisting of: survival fraction at a selected time cutoff, objective response rate, and clinical benefit rate.

10. The tool of claim 1 wherein the processor further accepts inputs of categories risks and uses the input selection of categories to locate the markers and the iso-preference boundary along the second axis of the display area.

11. The tool of claim 10 wherein categories are selected from the group consisting of: any adverse medical event, any adverse medical events over a predetermined grade threshold, and any subset of specific organ toxicities.

12. The tool of claim 1 wherein categories are selected from the group consisting of: direct cost to the patient and inconvenience or indirect cost to the patient.

13. The tool of claim 1 wherein the information for a given patient characterizing the risk-benefit preference by the patient is entered by an interactive control manipulable by a patient.

14. The tool of claim 1 wherein the processor receives patient-specific clinical information for a given patient and the treatment option risks or benefits for the treatment options may be based on the patient-specific clinical information.

15. The tool of claim 1 further providing a display of a multiple markers associated with a given medical treatment option over different times during a patient treatment with the given medical treatment option indicating a change in the risk-benefit of the given medical procedure informed by analysis of patient-specific data with respect to a given patient.

16. The tool of claim 15 wherein the processor further accepts inputs of medical procedure categories and provides a display of a set of multiple treatment options according to an input of a medical procedure category.

17. The tool of claim 1 wherein the processor receives a user-selectable maximum risk level and a minimum benefit level and wherein the display area displays markers only associated with treatment option benefits above the minimum benefit level and treatment option risks below the maximum risk level.

* * * * *